United States Patent [19]

Monroe et al.

[11] Patent Number: 5,919,130
[45] Date of Patent: Jul. 6, 1999

[54] VIDEO OTOSCOPE

[75] Inventors: Richard A. Monroe; David G. Perkins; Robert J. Wood, all of Syracuse, N.Y.

[73] Assignee: Welch Allyn, Inc., Skaneateles Falls, N.Y.

[21] Appl. No.: 08/818,422

[22] Filed: Mar. 17, 1997

Related U.S. Application Data

[63] Continuation-in-part of application No. 08/403,294, Mar. 14, 1995, abandoned.

[51] Int. Cl.$^6$ ..................................................... A61B 1/227
[52] U.S. Cl. .......................... 600/200; 600/129; 600/156; 600/182
[58] Field of Search ..................................... 600/109, 127, 600/129, 130, 156, 182, 200

[56] References Cited

U.S. PATENT DOCUMENTS

| | | | |
|---|---|---|---|
| 4,306,546 | 12/1981 | Heine et al. ............................. | 600/182 |
| 4,685,452 | 8/1987 | Riester .................................... | 600/200 |
| 5,239,984 | 8/1993 | Cane et al. .............................. | 600/112 |
| 5,329,936 | 7/1994 | Lafferty et al. ......................... | 600/109 |
| 5,345,926 | 9/1994 | Chikama ................................. | 600/200 |
| 5,363,839 | 11/1994 | Lankford ................................. | 600/112 |
| 5,527,261 | 6/1996 | Monroe et al. ......................... | 600/200 |

*Primary Examiner*—John P. Leubecker
*Attorney, Agent, or Firm*—Wall Marjama Bilinski & Burr

[57] ABSTRACT

A video otoscope includes an elongated body portion having a conically shaped insertion portion sized for insertion a predetermined distance into an ear canal. The insertion portion includes a tip opening and an interior having a lens system for focusing an optical image of a target onto a distally positioned imager each contained therein. The body portion includes an insufflation port to pressurize or apply a vacuum within the ear canal to allow stimulation of the tympanic membrane. In a preferred embodiment, a clear speculum releasably attached to the insertion portion transmits light to a target within the ear canal, while also allowing insufflated air to be reliably guided to the tip opening.

75 Claims, 10 Drawing Sheets

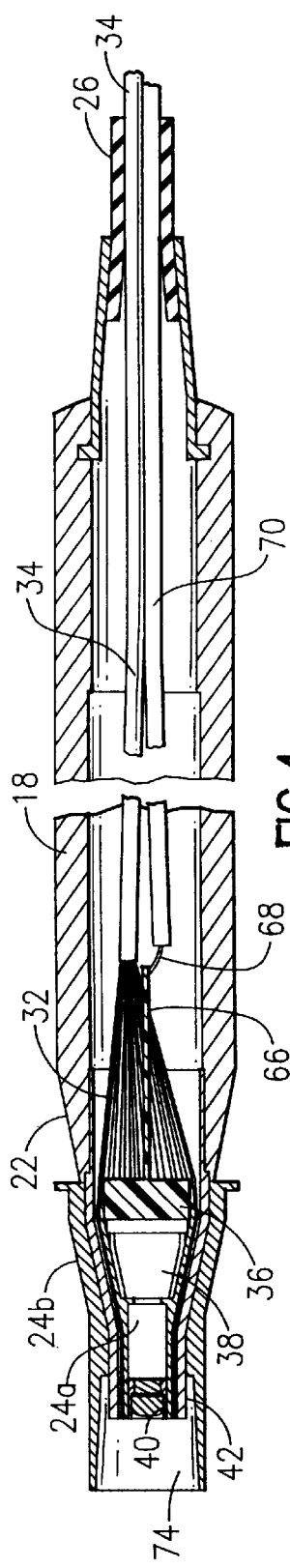
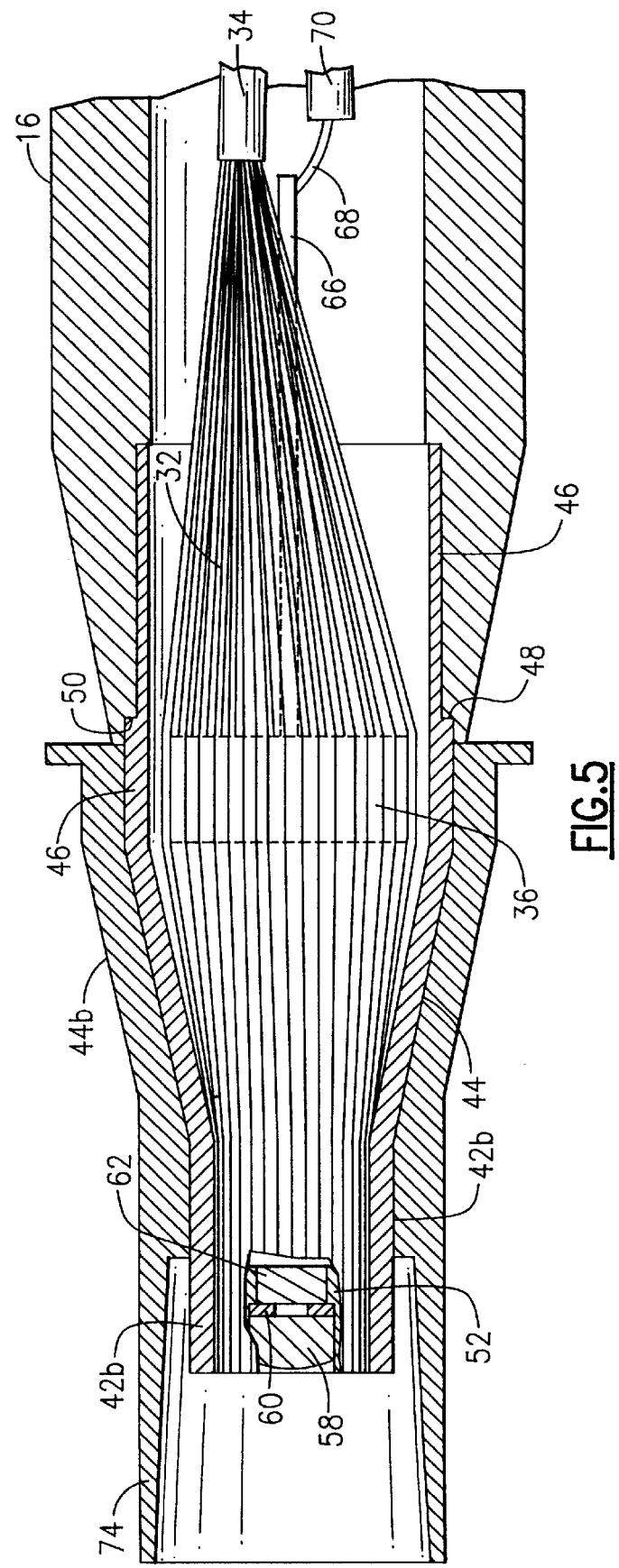
FIG.4
FIG.5

VIDEO OTOSCOPE

CROSS REFERENCE TO OTHER APPLICATIONS

This application is a continuation-in-part of U.S. Ser. No. 08/403,294, filed Mar. 14, 1995, now abandoned.

FIELD OF THE INVENTION

This invention relates in general to otoscopes and, in particular, to otoscopes having video capability. More specifically, this invention relates to video otoscopic apparatus having a distally mounted imager which may include insufflation capability and enhanced illumination.

BACKGROUND OF THE INVENTION

The art of otoscopes has been contributed to by a number of devices periodically proposed with the advancement of medical diagnostic devices. In recent years, video technology has been adapted for use with such diagnostic devices. Early attempts at providing video capability to otoscopes involved the use of a video adaptor and beam splitter which were mounted onto a conventional hand-held otoscope. This type of adaptor is illustrated in U.S. Pat. No. 5,239,984, issued to R. M. Cane et al. and entitled: "Hand-Held Opto-Diagnostic Instrument System". While providing an advancement to the art, the Cane et al. device is limited in that it relies on a beam splitter to divide light reflected from the object under investigation. Therefore, about one half of the illumination is directed to the eyepiece of the scope and is therefore lost. This type of attachment system also relies on being used with a standard otoscope or ophthalmoscope requiring a relatively large battery source for illumination.

More recently proposed video otoscopes include the type disclosed in U.S. Pat. No. 5,363,839 to J. D. Lankford. The Lankford device includes an otoscope head connected to a hand-holdable body portion. The imager or video camera of this device is positioned at the proximal end of the body portion. An elongated rod lens is employed to communicate light information from the distal tip of the device to the relatively distant proximally located video camera. Rod lenses, as currently known, are extremely expensive and fragile and are subject to breakage upon impact which might be ordinarily expected during use of this kind of device.

Certain endoscopes disclose positioning the CCD or other solid-state imager in the distal head. Examples include U.S. Pat. Nos. 4,639,772 to Sluyter, et al, 4,918,521 to Yabe, et al, 5,050,584 to Matsuura, and 5,379,756 to Pileski, et al. Each of the above patents describe optimal placement of the imager relative to a viewing optical system which focuses an optical image of the target onto the substrate of the imager. An illumination optical system projects light onto the target to allow viewing by the video camera through the viewing optical system. The illumination optical system, includes a bundle of optical fibers which are either disposed in a circumferential ring around the imager and viewing optical system as described in the '756 patent, or retained in a bundle and disposed parallel to the viewing optical system as described in the '521 patent to Yabe, et al.

Otoscopic examination is generally more unique than other endoscopic applications, however, for at least two reasons. First, the tympanic membrane is relatively large (approximately 6–7 mm for an average adult) as compared to the auditory canal (averaging about 4–5 mm). It is therefore desired to obtain as large a field of view as possible to effectively perform an examination. This was not previously achieved with so-called traditional optical otoscopes, as shown in FIG. 1. Use of a Hopkins or other rod lens assembly, however, provided a greater field of view, allowing the entirety of the tympanic membrane to be viewed all at once as shown in FIG. 2. With the advent of video otoscopes, such as described in the Lankford patent, it is still desired that a maximized field of view be achieved to allow the entire membrane to be viewed at once. It is also desired to attempt to replace the rod lens assembly, due to its inherent fragility and high cost.

Second, it is also highly desirable in otoscopic examinations to pressurize or apply a vacuum within the ear canal to stimulate the tympanic membrane, a feature commonly referred to as insufflation. Though contemplated in the Lankford patent, the otoscope described therein utilizes a proximally positioned electronic imaging element, which does not have the spatial constraint problems affecting an otoscope having a distally arranged image sensor, viewing optical system and illuminating optical system, respectively.

Therefore, there is a need to provide insufflation capability to a video otoscope having a CCD or other similar imager distally arranged within the insertion portion of the instrument to provide an enhanced field of view without use of a rod lens assembly, and done in a compact manner so as not to interfere with the illuminating or viewing optical systems.

SUMMARY OF THE INVENTION

It is a primary object of the present invention to improve otoscopes, particularly those having video capability.

It is another primary object of the present invention to provide insufflation capability in a video otoscope having a distally arranged video camera in order to allow a complete otoscopic procedure, without interfering with the illumination or real-time video capture of a viewed target.

Yet another object of the present invention is to employ a video otoscope having a camera head capable of being implanted into the ear canal to allow simultaneously viewing of both the ear canal and the tympanic membrane of a patient.

It is still yet a further object of this invention to position an imager as close as practicable to the distal end of the tip of a video otoscope to thereby increase the field of view of the otoscope, and without interfering with the ability to stimulate the tympanic membrane through insufflation.

An additional object of the present invention is to employ a video system to electronically process substantially all the light information reflected from a subject target object or area to thereby provide a video image on a monitor or other peripheral device.

Yet a further object of the present invention is to utilize a minimum amount of light in a video otoscopic system while still providing a bright readable image of the subject target object or area under investigation.

Still yet another object of this invention is to locate a miniature imager in the distal end of a video otoscope to thereby increase image quality and without interfering with insufflation.

It is yet an additional object of the present invention to eliminate the need of an elongated rod lens in a video otoscope.

These and other objects are attained in accordance with the present invention wherein there is provided according to a preferred embodiment a video otoscope for examining the interior of the ear canal, said otoscope comprising:

a body portion having an interior and a distal end, said distal end including a frusto-conical extension having a distal tip opening communicating with the body portion interior;

electronic imaging means disposed within the interior of said body portion;

an optical system including at least one optical element for focussing an optical image of a target viewed through said distal tip opening onto said electronic imaging means; and a speculum releasably mounted in overlaying fashion onto said conical extension, said speculum having a distal tip opening axially aligned with the tip opening of said extension along a defined viewing axis, said speculum and said extension being sized to allow location within said ear canal to a predetermined distance.

The video otoscope preferably includes insufflation means for allowing air under pressure to be directed through the distal tip opening of the speculum for stimulating the tympanic membrane of the ear canal being examined. The insufflation is directed from a first port into the interior of the body portion and is directed through a second port, either located according to one embodiment on the conical extension separately from the tip opening, or alternately through a discontinuous portion in a ring of optical illuminating fibers circumferentially disposed in the extension tip opening. The illumination of a target is improved by using a speculum made from a light transmissive material, such as polycarbonate, which directs the light from the fiber bundle or other light transmittance means directly through the body of the speculum.

In accordance with one aspect of the present invention, a lens cell is positioned within the conical extension for focussing an image of the target object or area on a focusing plane situated within the distal end of the body portion. A solid state or other form of imager is secured within the tip segment and behind the lens cell of the present video otoscope. According to another aspect of the present invention, the imager has an imaging plane that is coplanar with the focusing plane of the lens cell. A circuit board is connected to the imager which extends into the elongated body portion and includes processing circuitry for converting a raw video output signal from the imager into a monitor ready standard format signal suitable for displaying the image of the target object or area on a monitor or by utilizing the video signal by means of another peripheral device, such as a video printer, a computer or other known display interface.

The present video otoscope is intended to be used in conjunction with a video otoscopic system, such as illustrated in FIG. 3. This system generally includes a video otoscope in accordance with the present invention, a power supply and lighting unit for transmission of power and light inputs to the tip segment of the otoscope, and a video peripheral device, such as a video monitor for displaying and/or otherwise utilizing a video signal of a visual image of the target object or area undergoing the inspection or diagnosis. The present video otoscope, as used in this system, also includes a flexible conduit for carrying light and power from the power supply and lighting unit to the tip segment. The flexible conduit also transmits a monitor ready video signal from the imager through the video processing circuitry to the video monitor. Alternately, the video processing circuitry can be contained within the combined power supply and lighting unit rather than within the circuit board contained within the diagnostic instrument.

According to another aspect of the present invention, there is provided an otoscope for examining the interior of an ear canal, said otoscope comprising:

a body portion having a defined interior and respective open distal and proximal ends;

illumination means including a source of illumination and light transmittance means for transmitting light from said source of illumination to the distal end of said body portion; and a speculum mounted to said distal end for insertion into said ear canal, said speculum having a frusto-conical body including a distal end having a tip opening, said body portion including viewing means axially aligned with the tip opening of said speculum to allow viewing of a target therethrough when said speculum is attached, wherein said speculum is made from a light transmissive material allowing light from said distal end to be further transmitted from said light transmittance means through the body of said speculum to the distal end of said speculum for illuminating said target. The particular otoscope can be of the optical type, or can include video imaging means, such as an electronic sensor, such as a CCD or CMOS.

According to yet another preferred aspect of the present invention, an otoscope is provided for examining the interior of the ear canal, which comprises:

a body portion including an interior and opposite proximal and distal ends, said distal end including a frusto-conical distal extension having a distal tip opening;

a speculum releasably mounted to said distal end in overlaying fashion with said extension, said speculum having a frusto-conical shape including a distal tip opening axially aligned with the tip opening of said extension, said speculum being sized for insertion to only a predetermined distance into the ear canal;

viewing means for viewing a target of interest through said aligned distal tip openings along a defined viewing axis;

illumination means including a source of illumination and light transmittance means for transmitting light from said source of illumination to said distal end; and insufflation means for projecting air through the tip opening of said speculum, said insufflation means including a first port located on said body portion for allowing attachment thereto by a depressible pneumatic bulb or other means capable of projecting air or creating a vacuum into the interior of said body portion.

According to one embodiment, the insufflation means includes at least one second port extending through said distal extension of said body portion, said at least one second port for projecting air entering said interior from said first port through the tip opening of said speculum, said at least one second port disposed on the conical extension.

According to another embodiment, the insufflation means can be provided by at least one discontinuous portion of a ring of light emitting optical fibers circumferentially arranged about the viewing means in the distal tip opening of the conical extension.

An advantage of the present invention is that the conical shape of the distal extension and attached speculum prevent the head of the instrument from being positioned beyond a predetermined distance within the ear canal. The interior of the insertion portion is therefore very small, the present invention therefore providing a significant advance in the field by allowing an enhanced field of view for viewing, as well as insufflation capability without interfering with the viewing and/or illumination operations of the instrument.

Another advantage of the present invention is that a video otoscope can be compactly manufactured while maintaining the ability to provide insufflation without interfering with the viewing and illuminating aspects of the otoscope.

Yet another advantage of the present invention is that a CCD or other imager can be positioned in the conical distal extension of the otoscope, allowing the imager to be inserted into the ear canal, thereby providing an enhanced field of view, previously realized only in otoscopes having expensive and fragile rod lens assemblies.

Another advantage realized by the present invention is that improved illumination can be achieved using a clear light transmissive speculum to bring illumination more closely to bear on the target of interest.

Another advantage is that a clear light transmissive speculum as described provides a larger light transmission path than polished light emitting ends of an optical fiber bundle, therefore allowing more light to be directed to the target of interest without additional focusing required.

Further objects, features, and advantages of the present invention will be apparent from the following Detailed Description of the Invention when read with the accompanying drawings.

BRIEF DESCRIPTION OF THE DRAWINGS

FIG. 4 is a side sectional view of a first embodiment of a video otoscope useful in the depicted system of FIG. 3;

FIG. 5 is an enlarged partially broken away sectional side elevational view of the distal tip portion of a video otoscope of FIGS. 3 and 4;

FIG. 8 is a pictorial representation of the imager of the video otoscope of FIG. 7 in relation to a video display monitor and an ear canal undergoing diagnosis;

DETAILED DESCRIPTION OF THE INVENTION

Figure 3:
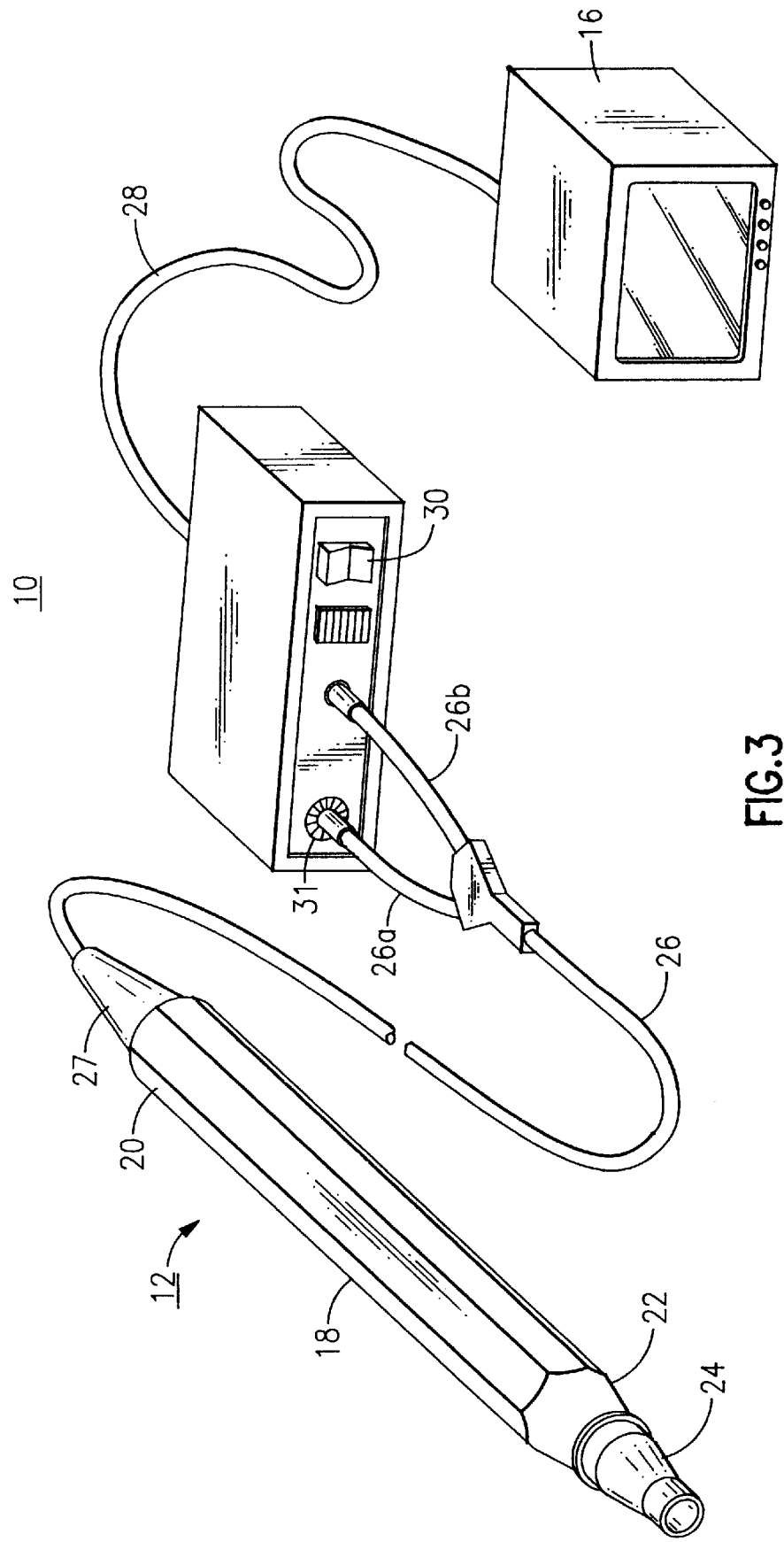
FIG. 3 is a perspective view of a video otoscopic system according to a first embodiment of the present invention.

Referring now to FIG. 3, there is shown a video otoscope system 10 in accordance with a first embodiment of the present invention. The system 10 includes a video otoscope 12, a combined power supply and lighting unit 14, and a video peripheral device. In this and each of the following embodiments described herein, a video display monitor 16 is used as the peripheral device, though it will be readily apparent that other peripheral devices, including but not limited to, video printers, video tape players, and personal computers can also be utilized.

The video otoscope 12 includes an elongated housing or body portion 18 having a substantially hollow interior and proximal and distal ends 20, 22. The distal end 22 of the elongated body portion 18 is provided with a substantially frusto-conically shaped distal extension 24 which is sized for positioning within an ear canal undergoing inspection or diagnosis. The substantially conical shape is essential with otoscopic instruments to prevent overextension of the inserted tip segment into the ear canal. The distal extension 24 according to this embodiment includes an inner tip housing 24a, FIG. 4, retained within an outer tip housing 24b, FIG. 4, each of which are described in greater detail below.

Still referring to FIG. 3, the video otoscope 12 is connected to the power supply and lighting unit 14 by means of a flexible umbilical cable 26 having one bifurcated end having a pair of connector segments 26a and 26b for interconnecting to receptacles (not shown) provided on the exterior of the unit 14. The proximal end 20 of the elongated body portion 18 is provided with a strain relief 27 to allow relative movement between the housing 18 and the umbilical cable 26. The power supply and lighting unit 14 is in turn, interconnected to the video display monitor 16 by a separate connector cable 28. An ON/OFF toggle or rheostat switch 30 on the front of the power supply and lighting unit 14 controls power to a metal halide arc discharge lamp (not shown) or other suitable light source positioned within the unit. A light control knob 31 separately controls the level of illumination. A connector cord of standard design (not shown) is connected at one to an AC power source, such as a wall outlet, the power supply unit 14 having circuitry therein for converting to DC power in a manner commonly known to those in the field.

With reference now to FIGS. 3–5, the lamp (not shown) contained within the power supply and lighting unit 14 supplies illumination for the above described video otoscope 12. With reference to this particular embodiment, a plurality of light-emitting optical fibers 32, (partially shown) are shaped into a bundle 34 and retained within the umbilical cable 26 and further into light connector 26b so as to immediately be proximate with flexible umbilical cable 26. The lamp (not shown) provided in the power supply and lighting unit 14 is situated immediately in front of the end of the connector segment 26b, as is described in greater detail in co-pending and commonly assigned U.S. Ser. No. 08/535, 651. In this manner, when the ON/OFF toggle switch 30 is activated, light is directed into the fiber bundle 34. As described in greater detail below, the bundle of fibers 34 extend through the umbilical cable 26 and are fanned out in the distal end 22 of the elongated body portion 18 in a circumferential or annular space formed between the inner tip housing 24a, and the outer tip housing 24b of the distal extension 24.

The interior of the elongated body portion 18 of the present embodiment is provided with a miniature video camera 35, such as a solid-state imager 36; e.g. a CCD or CMOS. It will be readily apparent from the discussion which follows that any miniature imager of known type can be substituted. According to this particular embodiment, a cone-shaped piece or block of high index glass 38 is positioned in front of the imager 36. The glass block 38 is preferably bonded to the imager 36 by means of an ultraviolet epoxy glue. This type of glue, when set, will not obscure light passing through the glass block 38 onto the imager 36. As will be seen from succeeding embodiments, however, the proximity of the imager 36 to the distal end 22 of the otoscope obviates the need for the block 38.

Figure 7:
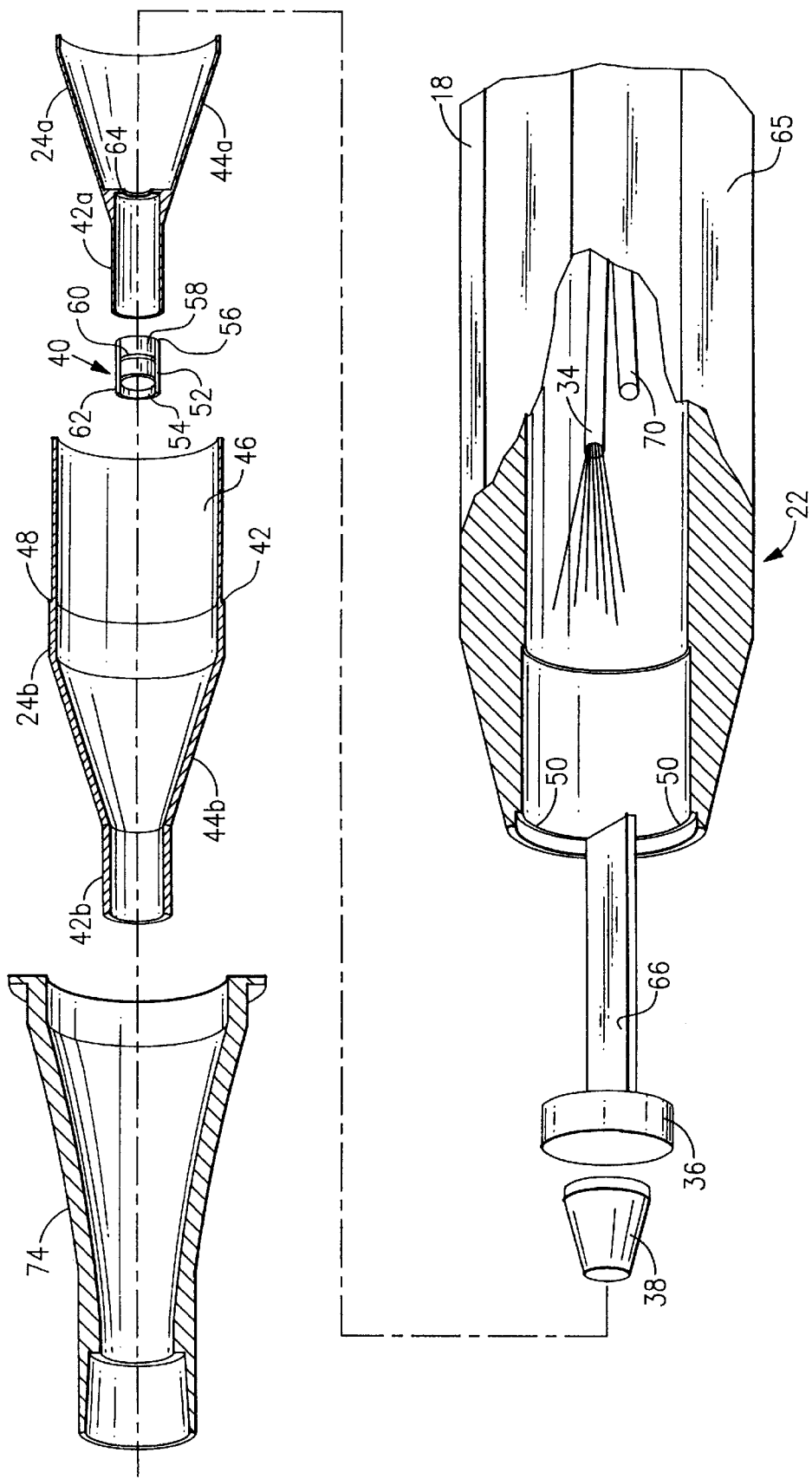
FIG. 7 is an exploded pictorial view of the components employed in the distal extension of the video otoscope of FIGS. 3–6.

Referring now to FIGS. 4 and 7, a lens cell 40 is positioned within a substantially cylindrical distal end segment 42a of the inner tip housing 24a. The inner tip housing 24a includes the cylindrical distal end segment 42a which extends proximally into a substantially conical segment 44a. The outer tip housing 24b similarly includes a substantially cylindrical distal end segment 42b which also extends proximally into a substantially conical segment 44b and further extends into a segment 46 of constant diameter. In this preferred embodiment of the present invention, an annular ridge 48 is formed around the exterior of the segment 46 as shown which engages a mating annular seat 50, which is formed in the open distal end 22 of the elongated body portion 18.

Still referring to FIGS. 4 and 7, the lens cell 40 includes a lens housing 52 having a distal end 54 and a proximal end 56. The lens housing 52 contains the imaging optics for the lens cell 40. These imaging optics include an objective lens 58 situated within the proximal end 56 of the lens housing 52, an aperture stop 60 positioned in front of the objective lens 58, and a plano lens 62 located in front of the aperture stop 60 and within the distal end 54 of the lens housing 52. The purpose of the lens cell 40 is to focus an image of the target of interest onto the substrate 37, FIG. 8, of the imager 36, as is described below with reference to FIG. 8.

Continuing to describe the structure of the particular otoscope 10, and as illustrated in FIG. 7, the cylindrical segment 42a of the inner tip housing 24a includes a bottom annular rim 64. Upon assembly of the lens cell 40 with the inner tip housing 24a, the lens cell 40 is press fit into the cylindrical segment 42a until it seats against the bottom annular rim 64. Upon further assembly of the video otoscope 12, the outer tip housing 24b is press fit into the distal end 22 of the body portion 18 so that the annular ridge 48 seats against the annular seat 50, as shown in FIG. 7. When using the described video otoscope 12, the greater part of the elongated body portion 18, i.e. that part excluding the extension 24 and the distal end 22, forms a handle segment 65 ideally suited for holding in the hand of a practitioner. As should be apparent, the diameter of the cylindrical segment 42 is smaller than the diameter of the handle segment 65 since the cylindrical segment 42 is for positioning within an ear while the handle segment 65 is designed for a comfortable fit in the practitioner's hand. Each are preferably shaped and/or marked conveniently so that the proper orientation of the insertion portion is apparent to the user.

As shown in FIGS. 7 and 8, the imager 36 is directly connected to a circuit board 66. The circuit board 66 extends into the distal end 22 of the elongated body portion 18. The circuit board 66 is provided with processing circuitry for converting a raw video output signal from the imager 36 into a monitor-ready standard format signal suitable for displaying an image of the ear canal on the monitor 16. This standard signal is contemplated to include, for example, a standard NTSC, PAL, or SECAM color video signal.

The circuit board 66 is connected to a series of parallel transmission lines or conductors 68 which relay the video signal proximally through the umbilical cable 26 and into the power supply and lighting unit 14, which in turn relays the signal to the video display monitor 16. The transmission lines 68 are contained in a cable 70 that extends into the umbilical cable 26 and further into connector segment 26a shown in FIG. 3. It should be noted that the processing circuitry should not be limited to the plug-in connector, for example, circuitry could be contained within the peripheral device 16 or the combined light box/power supply 14.

Figure 6:
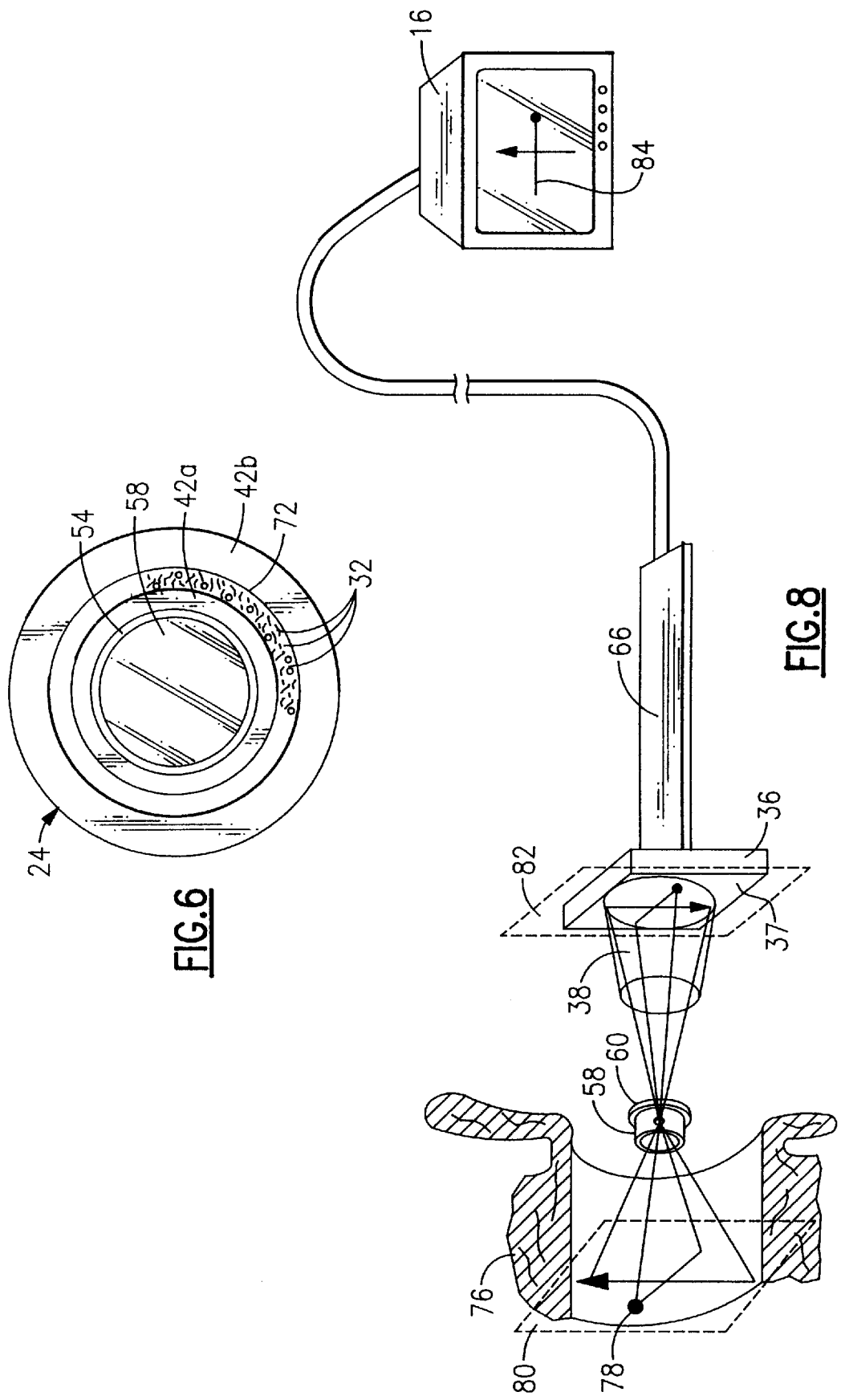
FIG. 6 is an enlarged front elevational view of the distal extension of the video otoscope of FIGS. 4 and 5 illustrating the annular ring of illumination around the lens cell.

With specific reference now to FIG. 6, there is shown an enlarged front elevational view of the distal extension 24. As illustrated, the plano lens 62 is contained within the lens housing 54 which in turn, is surrounded by the cylindrical distal end segment 42a of the inner tip housing 24a, FIG. 4. Further to the assembly discussion above, when the inner tip housing 24a, FIG. 4, is press fit into the outer tip housing 24b, FIG. 4, the plurality of optic fibers 32 is fanned out therebetween to form an annular ring of fiber ends 72. In this manner, when the distal extension 24 is positioned within an ear, the ear canal is optimally illuminated. In accordance with hygienic use of the video otoscope 12, a disposable plastic tip or speculum 74 is provided as a protective covering for the outer tip housing 24b, the speculum including a set of interior ridges (not shown) for engaging a slot in the outer tip housing 24b to retain the speculum in a bayonet-type support. This support is described in greater detail in copending and commonly assigned U.S. Pat. No. 4,380,998, issued to Kieffer, et al, the entire contents of which are hereby specifically incorporated by reference. In operation, a supply of disposable plastic tips 74 are provided, so that after each use a clean safety speculum 74 can be used. Similarly, the safety speculum 74 is also defined by a substantially frusto-conical section which overlaps the outer tip housing 24b, FIG. 4, to allow straightening of the ear canal, the shape preventing overextension therein.

The imaging provided by the particular video otoscope 12 will now be described with reference to FIG. 8. As represented therein, the otoscope 10 is positioned such that the outer tip housing 24b, FIG. 7, preferably covered by the conical safety speculum 74, FIG. 7, is positioned within the ear canal 76. A target object or area 78 which is the subject under investigation by the practitioner, is contained within an object plane 80. The lens cell 40 is positioned so that the object 78 in the object plane is in focus. Light reflected from the object 78 will pass through the aperture stop 60 and fall in focus and inverted onto a focusing plane 82, as well known in the art. Any light incident on the substrate 37 of the imager 36 is converted to raw video information on a pixel-by-pixel basis. In the video otoscope 12, the substrate 37 of the imager 36 is positioned so that it is coplanar with the focusing plane 82, also as is commonly known. In this manner, an image 84 of the object 78 will be in focus on the video display monitor 16.

Figure 9:
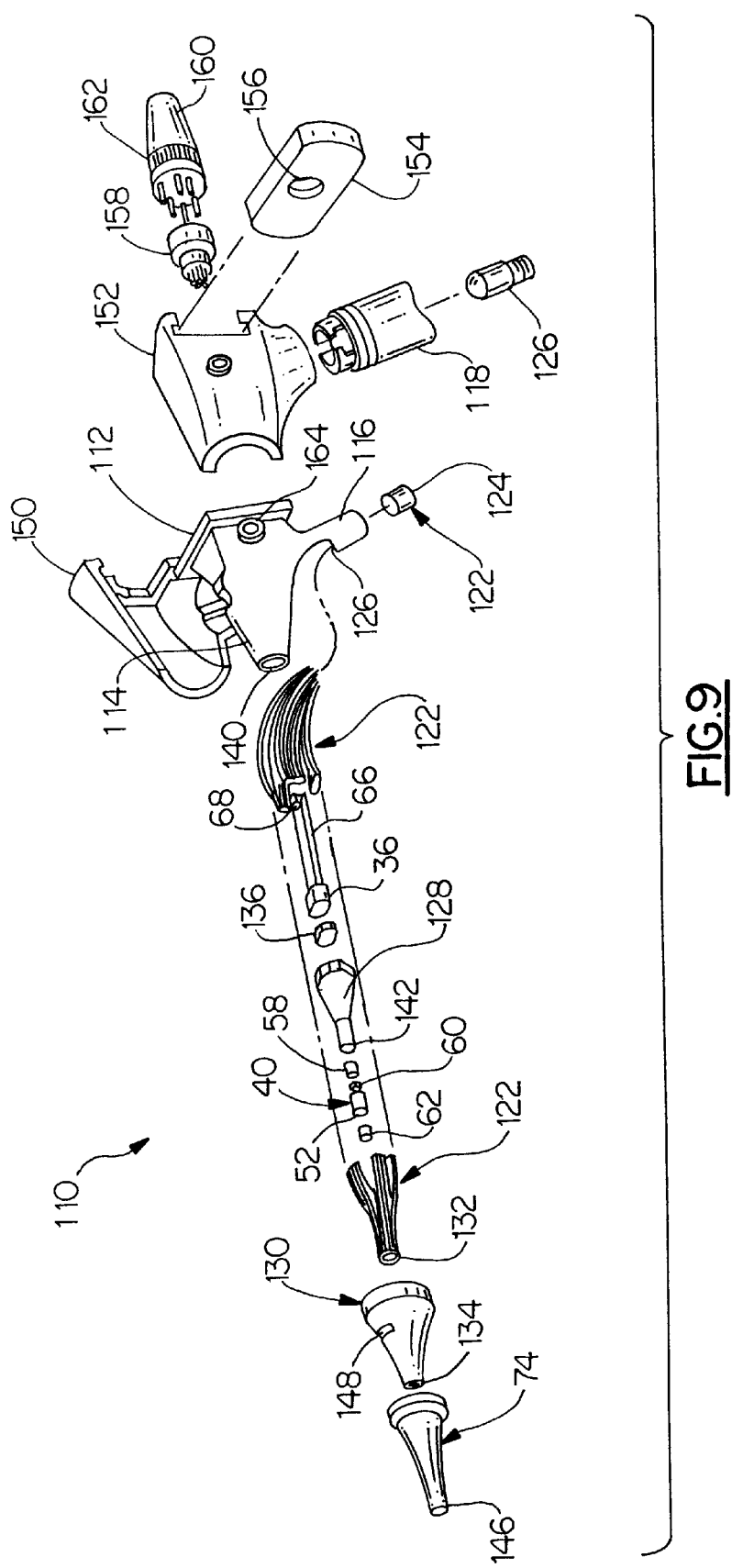
FIG. 9 is an exploded partial perspective view of a video otoscope according to a second embodiment of the present invention.
Figure 10A:
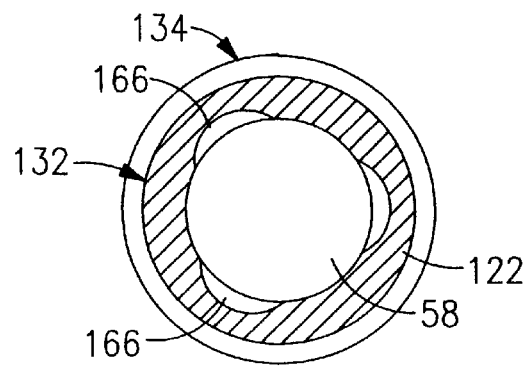
FIGS. 10(a), 10(b) and 11(a), 11(b) are partial front diagrammatic views of the distal tip of the video otoscope of FIG. 9 depicting separate embodiments for an insufflation air path.
Figure 10B:
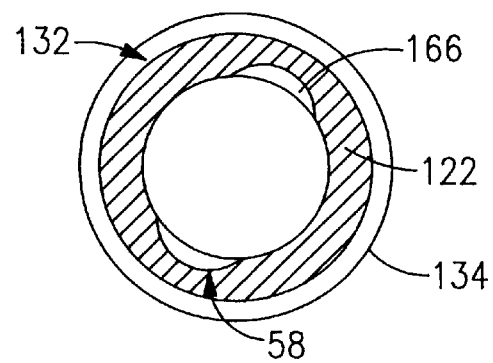
Figure 11A:
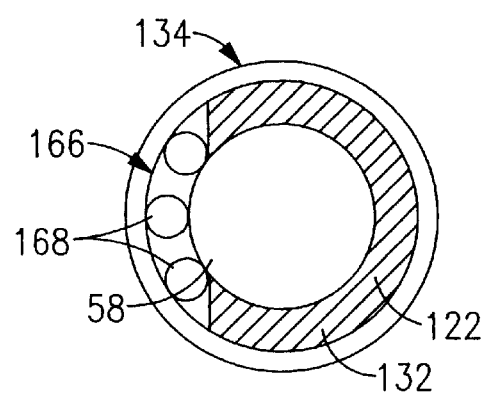
Figure 11B:
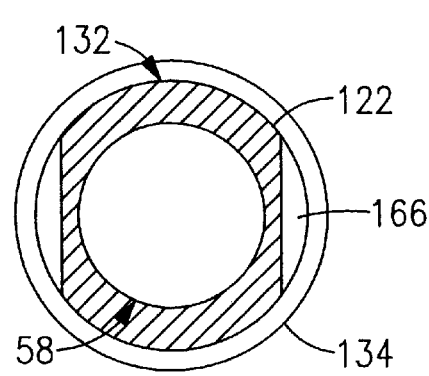

Referring now to FIGS. 9–11, a second embodiment of a video otoscope in accordance with the present invention will now be described. For purposes of clarity, similar parts will be labeled with the same reference numerals. Referring specifically to the exploded view depicted in FIG. 9, the video otoscope 110 according to this embodiment is also a hand-held device which is generally useful in the system of FIG. 3 having a body portion 112 including a substantially frusto-conical distal end or extension 114. A pair of substantially conical tip housings 128 and 130 are attached in overlaying relationship to the distal extension 114 of the body portion 112, each having a hollow interior specifically sized for retaining a number of components as now described in a manner similar to the first embodiment above.

In the otoscope of this embodiment, the body portion 112 is of a substantially trapezoidal shape and includes a hollow interior. A necked portion 116 extends from the bottom of the body portion 112 which is fitted into a depending handle portion 118, (shown partially in FIG. 9) allowing the otoscope 110 to be hand-held. Such handle portions are well known, as described in U.S. Pat. No. 5,239,984, and include a halogen bulb 120 for providing a light source transmitted through a bundle of optical fibers 122. The fiber bundle 122 is a molded epoxied arrangement having polished ends 124 placed in proximity with the halogen lamp 120 which extend through an opening 126 in the necked portion 116 and are fanned out and directed into the annular space between the inner and outer tip housings 128, 130. A plurality of polished light emitting ends, preferably forming a continuous ring 132 are disposed substantially coterminous with the tip opening 134 of the outer tip housing 130 when the inner tip housing 128 is press fitted into the interior of the outer tip housing when the otoscope 110 is finally assembled.

The conical inner tip housing 128 retains a lens cell 40, such as previously described, having an objective lens 58, an aperture stop 60 and a plano lens 62 arranged within a lens housing 52. The lens cell 40 focusses an optical image onto a solid-state or other known imager 36, each contained within the inner tip housing 128 in substantially the same manner previously described. According to this embodiment, a thin glass or plastic cover plate 136 effectively replaces the cone-shaped piece of index glass 38, FIG. 8, previously described in the first embodiment, thereby allowing the imager 36 to be positioned substantially more distal within the inner tip housing 128, and ultimately closer to the tympanic membrane during an otoscopic examination to provide an enhanced field of view.

As in the preceding, a circuit board 66 is attached in a known manner to the rear of the imager 36 for transmitting an electrical signal via transmission lines or conductors 68 from the imager to a proximally located electrical connector 158.

The body portion 112 includes a distal opening 140 from the hollow interior which is coaxially arranged with the respective tip openings 142, 134 of the inner and outer tip housings 128, 130, as well as the tip opening 146 of a frusto-conical safety speculum 74 attached in overlaying fashion to the exterior of the outer tip housing used to straighten the soft tissue of the ear canal for viewing the tympanic membrane. The outer tip housing 130 includes a radial slot 148 for engaging an interior ridge (not shown) of the safety speculum 74 to releasably allow attachment to the conical tip housing, preferably in the manner described in the previously incorporated U.S. Pat. No. 4,380,998. As described in the preceding, the insertion portion of the otoscope, including the speculum 74 are also conically shaped to prevent overextension into the ear canal.

A pair of formed housing members 150, 152 sandwich the exterior of the body portion 112 and interconnect the body portion to the handle portion 118, covering the necked portion 116 and formed fiber optic bundle 122. A rear plate 154 retained by the housing members 150, 152 includes an opening 156 sized for retaining the proximal electrical connector 158 and umbilical cable 160. The umbilical cable 160 includes a corresponding electrical connector 162 at one end extending to a power supply (not shown) and video peripheral device (not shown) in a manner similar to that of FIG. 3 so as to provide power input to the otoscope 110, and to allow a video signal to be transmitted to the peripheral device for display of a viewed target.

Figure 1:
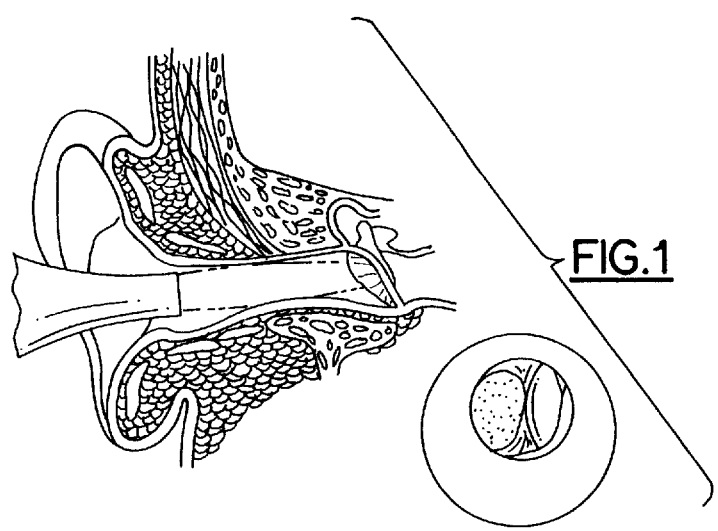
FIG. 1 is a pictorial elevational view, partially in section of a conventional otoscope according to the prior art used in observing the interior of an ear canal.
Figure 2:
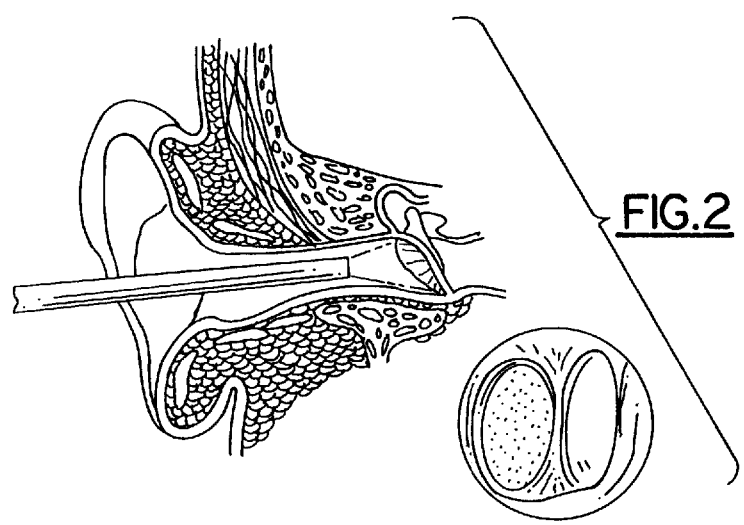
FIG. 2 is the pictorial elevational view of FIG. 1, depicting the insertion portion of a second otoscope utilizing a rod lens assembly in accordance with the prior art.
Figure 12:
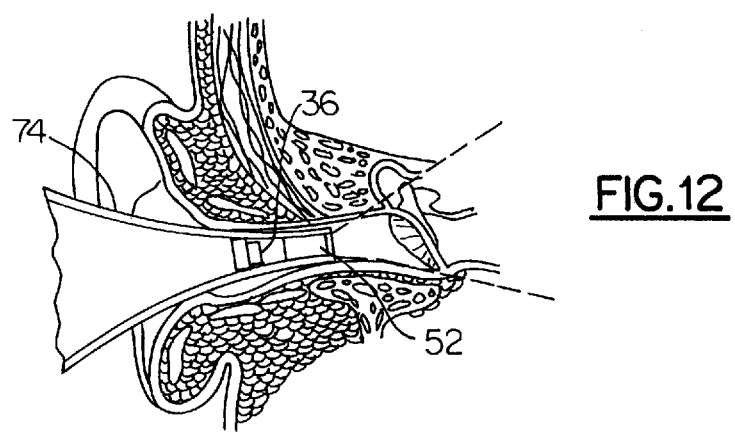
FIG. 12 is a pictorial elevational view of the video otoscope of FIGS. 9 and 10 relative to the ear canal as compared to those illustrated in FIGS. 1 and 2.

In use, each of the preceding embodiments allow positioning of the distal insertion portion of the video otoscope 110 into the ear canal without the use of a rod lens assembly, but because the imager 36 is located as far as practicable to the tip opening and actually within the ear canal, an enhanced field of view can now be realized, as is illustrated diagrammatically in FIG. 12, as compared to the prior art otoscopes previously referred to in FIGS. 1 and 2.

Referring back to FIG. 9, the video otoscope 110 also includes an insufflation port 164 extending through one of the housing members 152 and into the interior of the body portion 112. The port 164 is sized to accommodate a pneumatic bulb (not shown) attached thereto. The bulb is engaged with the port to pressurize or apply a vacuum into the interior of the body portion 112, as is known. Specific details relating to the insufflation port and the pneumatic bulb and their operation are provided in the previously referred to U.S. Pat. No. 5,363,839, to Lankford, the entire contents of which are incorporated by reference.

The interior of the body portion 112 is effectively sealed so that air under pressure will not escape through the top, bottom, sides or rear of the body portion 112. The only effective escape for the insufflated air is therefore through the distal tip opening 140. As distinguished from the '839 patent, however, the presence and tight spatial constraints presented by the components of the present embodiment retained in the inner and outer tip housings 128, 130 (ie: distally arranged imager 36, lens cell 40, and illumination bundle 122) prevents air from being directed through the tip opening 146 of an attached speculum 74 to stimulate the tympanic membrane. In addition, the epoxied bundle of optical fibers 122 fits tightly within the annular space defined between the inner and outer tip housings 128, 130, therefore also resisting the passage of air therethrough.

Therefore, and referring to the partial front elevational views of the otoscope of FIG. 10(*a*), a plurality of channel-like openings 166 are provided in the narrow annular space between the assembled inner and outer tip housings 128, 130, FIG. 9. As noted above, the fanned out bundle of optical fibers 122 are tightly engaged within this space, and because the fibers are epoxied together, a resistant barrier prevents air from escaping the otoscope 110 other than through the channels 166. The channel-like openings 166 extend through the entire length of the space between the inner and outer tip housings 128, 130, FIG. 9, and can be created, such as by use of a removable mold or fixture fitted into the annular space between the housings during assembly.

Any number of channels can be formed in order to form a sized path for the air to exit the speculum 74. Alternate configurations are illustrated in FIGS. 10(*b*), 11(*a*), and 11(*b*) in which the cylindrical bundle 122 of illuminating optical fibers can be locally interrupted in order to provide an insufflation air path. It should be readily apparent to those of ordinary skill in the field that other similar configurations can be imagined.

Referring to FIG. 11(*a*), at least one hollow tubular member 168 can be introduced into any or all of the channels 166. Preferably, the member includes a length dimension which extends into greater proximity with the insufflation port 164, FIG. 9.

Figure 13:
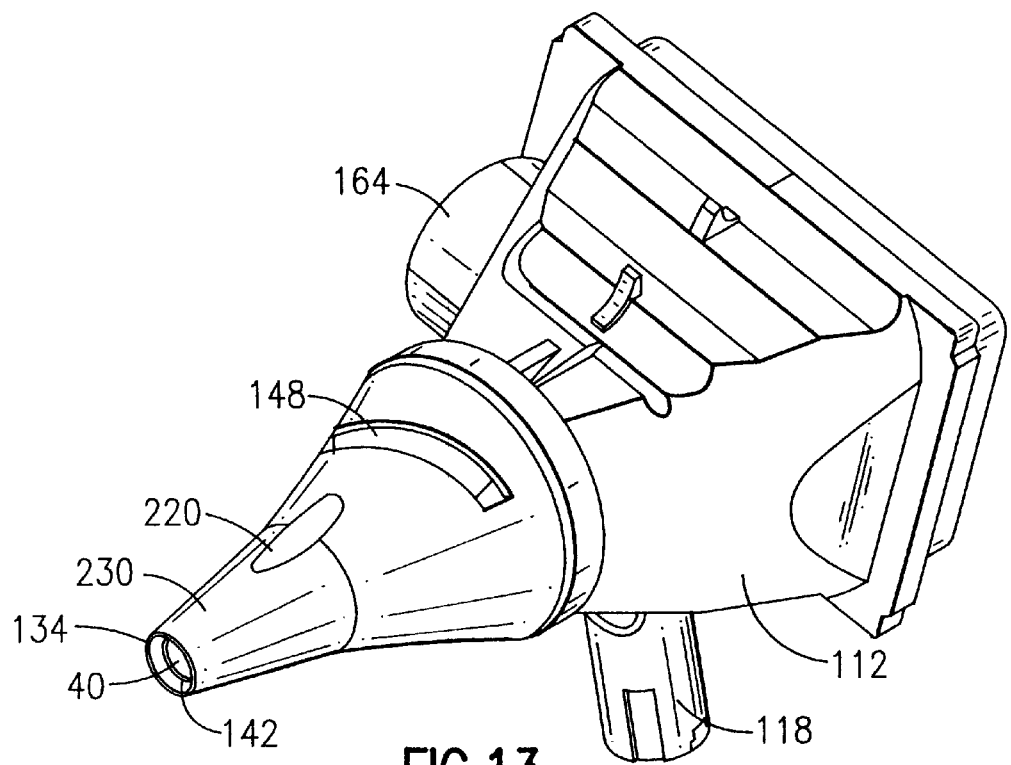
FIG. 13 is a partial top perspective view of the distal tip of a video otoscope made in accordance with a third embodiment of the present invention.
Figure 14:
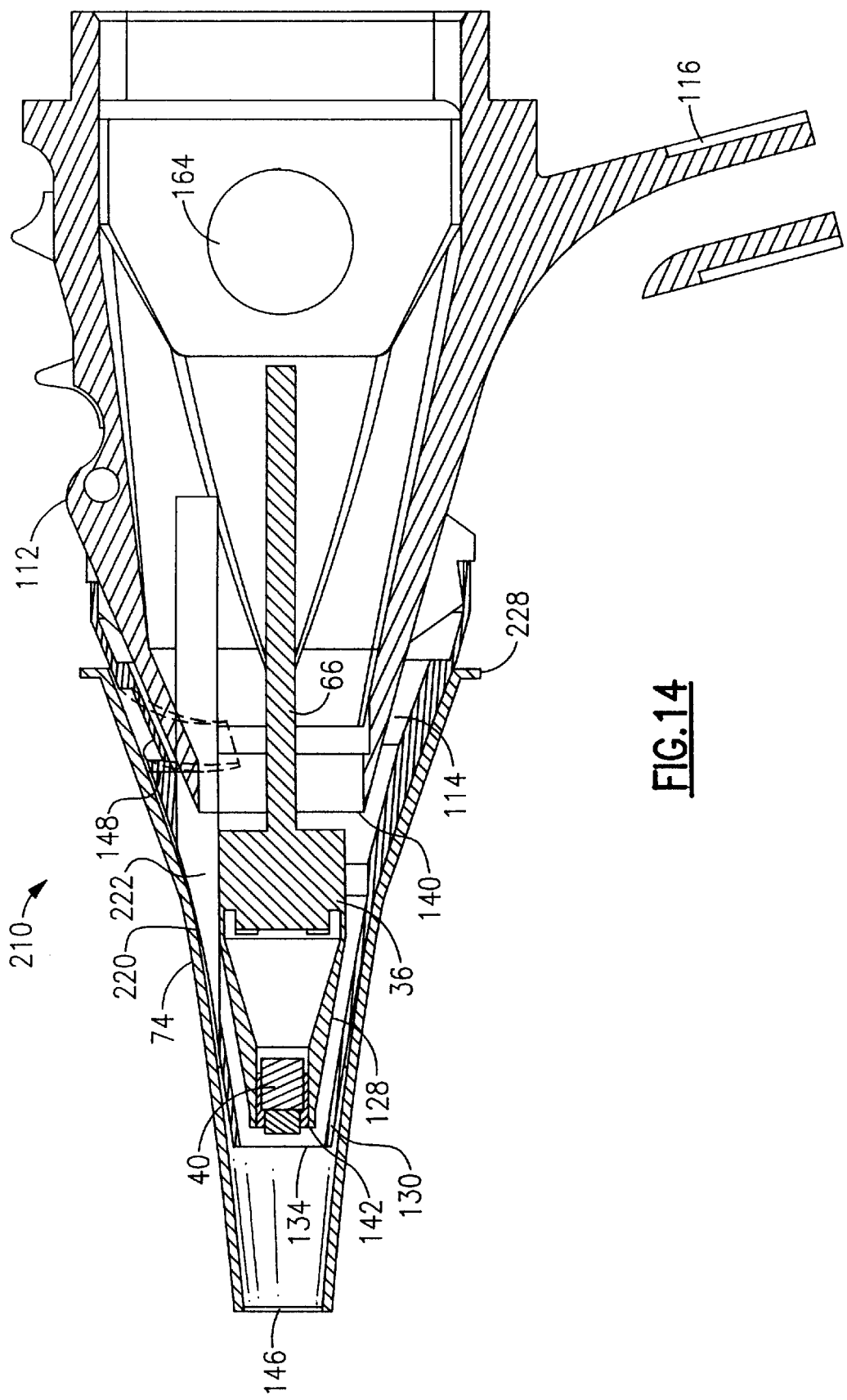
FIG. 14 is a partial sectional view of the distal tip of FIG. 13.

A video otoscope 210 in accordance with a third embodiment of the present invention is herein described with reference to FIGS. 13 and 14. Similar parts as those used in the preceding embodiments will be labeled with the same reference numerals for the sake of clarity.

In general, the video otoscope 210 of this embodiment is quite similar to that described in the preceding embodiment, including a body portion 112 as previously described having a distal end or extension 114 having integrally attached thereto an inner and outer tip housing 128, 230 placed in overlaying relationship therewith. The distal extension 114, inner tip housing 128 and outer tip housing 130 are each substantially conical in shape and include tip openings 140, 134, and 146, respectively. The inner tip housing 128 includes an interior sized for retaining an imager 36 and a viewing optical system, including a lens cell 40 like that previously described. The body portion 112 also includes an insufflation port 164, also as previously described, allowing interconnection to a depressible pneumatic bulb (not shown). A circuit board 66 extends proximally from the imager 36 for transmitting an electrical signal generated by the imager to video processing circuitry (not shown) which processes a monitor-ready video signal, preferably for subsequent display.

To complete the description of this particular embodiment, the remainder of this particular otoscope 210 is literally identical to that previously described in FIG. 9, and can form a part of the system as illustrated in FIG. 3. The outer tip housing 230 includes a curved radial slot 148 for accommodating an overlaying safety speculum 74 in the manner described in previously incorporated U.S. Pat. No. 4,380,998. The safety speculum 74 is not shown in FIG. 13 for the sake of clarity regarding other particular features of the present invention. Though also not shown in this particular embodiment, a plurality of light transmitting optical fibers extends from a necked portion 116 and include polished light emitting ends which are preferably fanned out into a substantially circular ring disposed in the annular space provided between the inner and outer tip housings 128, 230, also as previously described. The fibers are preferably tightly or densely packed together and epoxied, providing an effective seal.

The outer tip housing 230 according to this embodiment includes a circumferential slot 220 extending into the interior of the body portion 112 and providing an air path for the insufflated air entering through the port 164. A hollow tubular member 222 is inserted into the through port 220 and a corresponding discontinuance or channel (not shown) in the fiber optic bundle, extending longitudinally into the body portion 112 and adjacent the insufflation port 164. Because the fiber optic bundle is not as tightly packed away from the distal portion of the otoscope, the fibers can be more easily separated away in order to provide sufficient clearance for the tubular member 222. The port 220 is preferably located such that the insertion of the tubular member 222 does not interfere with the axial compact placement of the imager 36 and the inner tip housing 128 within the insertion portion of the otoscope.

In use the distal extension 114, including the overlaying safety speculum 74, is inserted into the ear canal as previously shown in FIG. 12. An image of the interior of the canal is visible due to the lens cell 40, which focusses an image of the target onto the image plane of the imager 36. The imager 36 then converts the optical signal of the target into an electrical signal processed by the circuit board 66 and transmitted in the manner previously described to the video monitor 16, FIG. 3, for display. Each of the above features are consistent with those commonly known in the field. Upon depression of an insufflation bulb (not shown) or other means attached to the insufflation port 164, a small quantity of air is projected into the interior of the body portion 112 and guided through the hollow interior of the tubular member 222, exiting the otoscope 210 through the speculum tip opening 146 to thereby stimulate the tympanic membrane. The interior of the body portion 112 is sealed, with the exception of the port 220, thereby preventing air from escaping the body portion other than as described. A rear circular base portion 228 of the safety speculum 74 seals directly against the exterior of the outer tip housing 130, thereby preventing insufflating air from escaping other than through the tip opening 146. In this manner, a more complete otoscopic examination is provided, with the compact placement of the distally located imager and lens system affording an enhanced field of view of the target of interest, and insufflation capability being adequately provided without interference with either the illuminating or viewing aspects of the otoscope, in this instance by positioning the port rearwardly (proximally) from the tip opening 146 as far as possible.

Figures 16A, 16B:
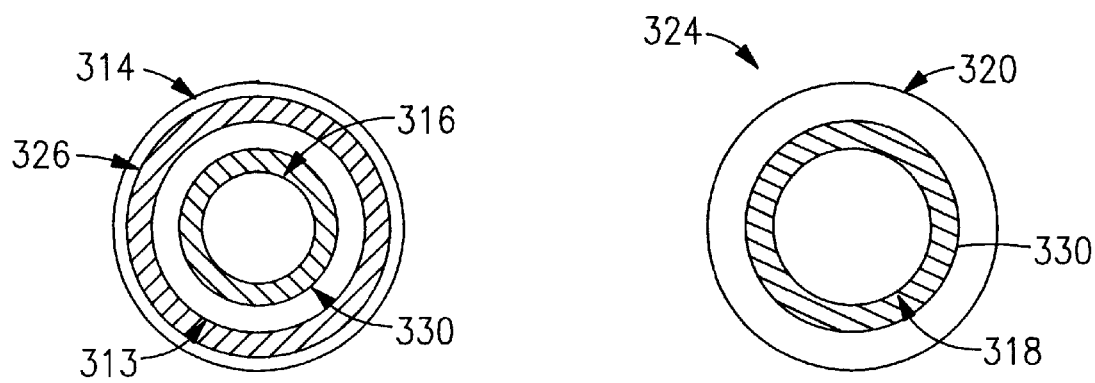
FIGS. 16(a) and 16(b) are partial front elevational views of the distal extension of the video otoscope of FIG. 15 and the distal end of the light transmissive speculum according to this embodiment, respectively.
Figure 15:
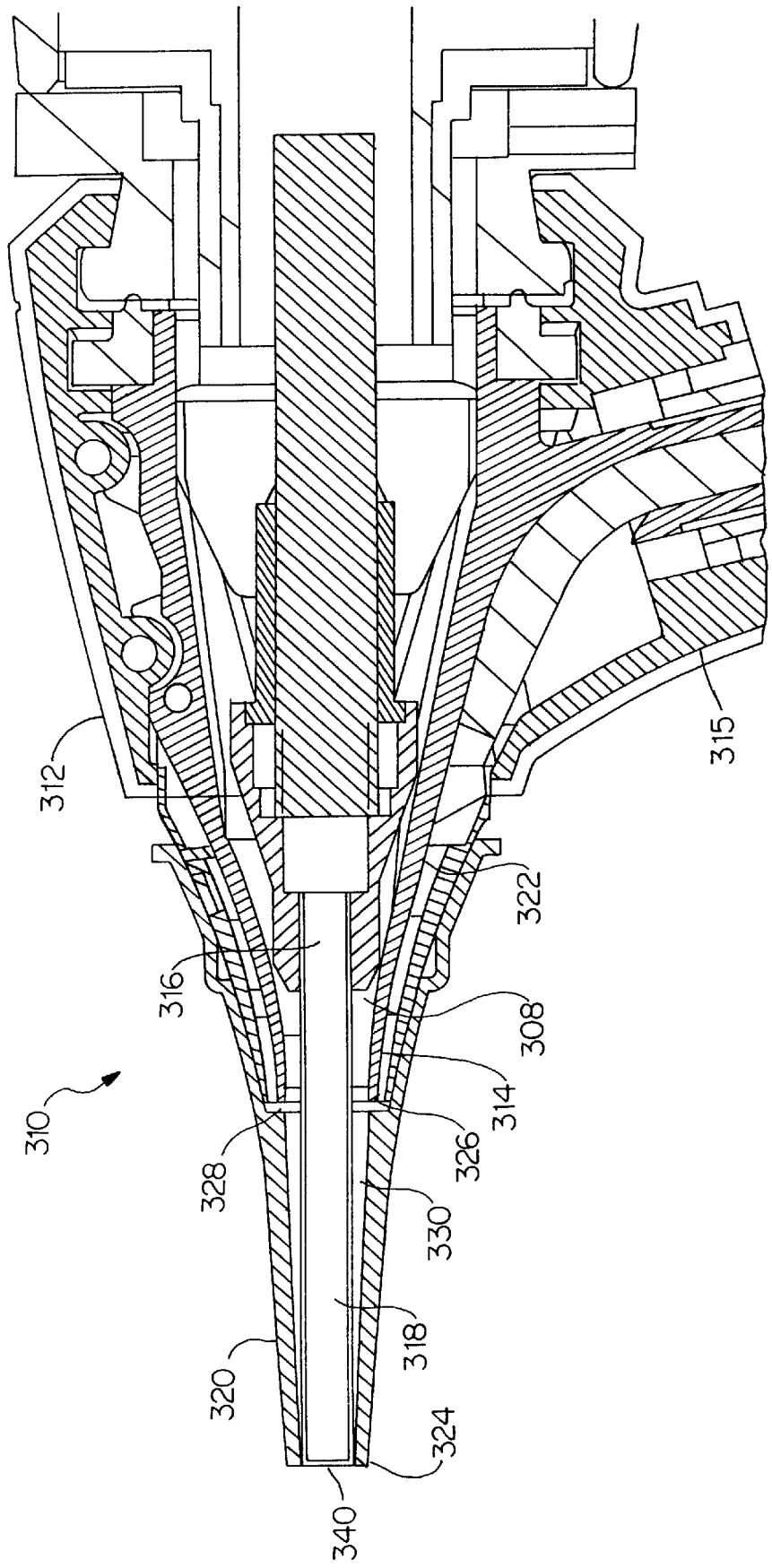
FIG. 15 is a sectional view of a video otoscope in accordance with a fourth embodiment of the present invention.

Referring to FIGS. 15, 16(a), and 16(b), a video otoscope 310 according to a fourth embodiment of the present invention will now be described. As in the preceding embodiments, similar parts are labeled with the same reference numerals for the sake of clarity. The otoscope 310 of this embodiment includes a body portion 312 having a distal conically shaped extension 308. A rod lens assembly 316 instead of a lens cell 40, FIG.7, as previously described, focusses an optical image onto an imager contained within the interior of the otoscope. The rod lens assembly 316 has an elongated distal rod end 318 extending from an outer tip housing 314 integrally attached in overlaying relationship to the distal tip segment 308. The outer tip housing 314 retains a speculum 320 in overlaying relationship thereto, the speculum being attached in a known manner, as previously described.

Referring to the sectional view of FIG. 15, a lamp (not shown) or other source of illumination is provided in the handle portion 315 (partially shown) of the instrument. A plurality of optical light emitting fibers 322 include polished ends (not shown) placed in proximity with the lamp (not shown) which are fanned out into a circular ring around the distal extension 308. Rather than extending the optical fibers 322 to the end of the rod lens assembly 316 and into the annular space between the speculum 320 and the distal rod lens end 318 in the manner previously described, the light emitting ends of the bundle 322 terminate at the end of the overlaying tip housing 314.

The speculum 320 according to this embodiment is made from a clear light transmissive material, such as polycarbonate. An intermediate circular engagement portion 328 of the speculum 320 having a generally flat surface which is generally perpendicular to the light emitting end of the fiber optic bundle 322 is brought into proximity with the remaining ends of the circular ring of the plurality of optical fibers which have fanned out. Light from the lamp (not shown) is transmitted through the light emitting ends of the optical fiber bundle 322 and conducted from the intermediate circular portion 328 through the length of the body of the speculum 320 in order to longitudinally direct the illumination through the speculum, exiting therefrom through a tip end 340.

Additionally, each of the surfaces receiving light from the fiber optic bundle 322, including the tip end 340, can include a curvature to better focus or direct light relative to the target of interest. The speculum can also be made diffuse to insure the illumination is uniformly distributed.

Referring to the partial front elevational views of FIGS. 16(a) and 16(b), depicting the distal tip opening of the distal tip housing 314 and the tip opening of the speculum 320, respectively, the advantage realized by including a clear speculum 320 as described herein is that without the presence of the optical fiber bundle 322 between the inner and the outer tip opening, there is an adequately spaced air gap 330 to allow insufflating air to escape through the speculum tip opening 324. In addition, the illumination is also effectively transmitted directly to the tip end 340.

PARTS LIST FOR FIGS. 1–16(b)

10 system
12 video otoscope
14 power supply and lighting unit
16 video display monitor
18 body portion
20 proximal end-body portion
22 distal end-body portion
24 distal extension
24a inner tip housing
24b outer tip housing
26 umbilical cable
26a connector segment
26b connector segment
27 strain relief
28 connector cable
30 ON/OFF switch
31 light control knob
32 optical fibers
234 bundle
35 miniature video camera
36 solid-state imager
37 substrate
38 block
40 lens cell
42a cylindrical distal end segment (inner tip housing)
42b cylindrical distal end segment (outer tip housing)
44a conical segment (inner tip housing)
44b conical segment (outer tip housing)
46 constant diameter segment (outer tip housing)
48 annular ridge
50 annular seat
52 lens housing
54 distal end—lens housing
56 proximal end—lens housing
58 objective lens
60 aperture stop
62 plano lens
64 bottom annular rim
65 handle segment
66 circuit board
68 transmission lines or conductors
70 cable
72 ring of fiber ends
74 speculum
76 ear canal
78 object
80 object plane
82 focus plane
84 image
110 video otoscope
112 head portion
114 distal end or extension
116 neck portion
118 handle portion
120 halogen lamp
122 optical fiber bundle
124 polished ends
126 opening
128 inner tip housing
130 outer tip housing
132 continuous ring of light emitting fiber ends
134 tip opening
136 cover plate
140 tip opening
142 tip opening
146 tip opening
148 radial slot
150 housing member
152 housing member
154 rear plate
156 opening
158 electrical connector
160 umbilical cable
162 electrical connector
164 insufflation port
166 channels
168 tubular member
210 otoscope
220 circumferential slot
222 tubular member
308 distal extension
310 otoscope
312 body portion
314 tip housing
315 handle portion
316 rod lens assembly
318 elongated distal rod end
320 light transmissive speculum
322 bundle of optical fibers
324 tip opening
326 illuminating ring
328 rear circular portion
330 air gap
340 speculum tip end While this invention has been described in detail with reference to a certain preferred embodiment, it should be appreciated that the present invention is not limited to that precise embodiment. Rather, in view of the present disclosure which describes the best mode for practicing the invention, many modifications and variations would present themselves to those of skill in the art without departing from the scope and spirit of this invention, as defined in the following claims.

What is claimed is:

1. A video otoscope for examining the interior of the ear canal, said otoscope comprising:

a body portion having an interior and a distal end, said distal end including a frusto-conical extension having a distal tip opening communicating with the body portion interior;

electronic imaging means disposed within the interior of said body portion;

an optical system including at least one optical element for focusing an optical image of a target viewed through said distal tip opening onto said imaging means; and a speculum releasably mounted in overlaying fashion onto said frusto-conical extension, said speculum having a distal tip opening axially aligned with the tip opening of said extension along a defined viewing axis, said speculum and said extension being sized to allow location within said ear canal to a predetermined distance and in which said electronic imaging means is disposed within said frusto-conical extension.

2. A video otoscope as recited in claim 1, including insufflation means for allowing air under pressure to be directed through the distal tip opening of said speculum for stimulating the tympanic membrane of said ear canal.

3. A video otoscope as recited in claim 2, wherein said insufflation means includes a first port located on said body portion sized for allowing attachment thereto by a depressible pneumatic bulb, said bulb being capable of projecting air into the interior of said body portion.

4. A video otoscope as recited in claim 3, wherein said insufflation means includes at least one second port extending through said frusto-conical extension into the interior of said body portion, said at least one second port being separately disposed on said frusto-conical extension from said distal tip opening to allow air entering said interior from said first port to be directed to the speculum tip opening.

5. A video otoscope as recited in claim 4, including at least one tubular member sized for fitting within said at least one second port and extending rearwardly toward said first port for directing air therefrom toward the speculum tip opening.

6. A video otoscope as recited in claim 3, including illumination means comprising a source of illumination and light transmittance means for transmitting light from said source of illumination through the interior of said body portion to the speculum tip opening.

7. A video otoscope as recited in claim 6, wherein said light transmittance means includes a bundle of optical fibers, said bundle of optical fibers including light emitting ends fanned out into a ring-like configuration around said optical system in the tip opening of said frusto-conical extension.

8. A video otoscope as recited in claim 7, including sealing means for sealing said bundle of optical fibers together for preventing the passage of air therethrough.

9. A video otoscope as recited in claim 7, wherein said ring of optical fibers includes at least one discontinuous portion extending rearwardly into the interior of said body portion, said at least one discontinuous portion forming a channel for allowing insufflated air to be directed through the tip opening of said extension.

10. A video otoscope as recited in claim 9, wherein said ring of optical fibers includes a pair of equally spaced discontinuous portions.

11. A video otoscope as recited in claim 10, including at least one hollow tubular member for fitting in at least one of said discontinuous portions, said at least one tubular member extending rearwardly from said tip opening of said extension toward said first port for directing insufflating air therethrough.

12. A video otoscope as recited in claim 9, including a hollow tubular member sized for fitting in said at least one discontinuous portion, said tubular member extending rearwardly from said tip opening of said extension toward said first port for directing insufflating air therethrough.

13. A video otoscope as recited in claim 3, wherein said optical system includes an objective lens assembly contained within said frusto-conical extension proximate to said tip opening, wherein the extension tip opening is substantially coterminous with the speculum tip opening.

14. A video otoscope as recited in claim 13, wherein said objective lens assembly is retained in an inner housing disposed within said frusto-conical extension.

15. A video otoscope as recited in claim 14, wherein said electronic imaging means includes an electronic sensor, said sensor being distally disposed in said inner housing proximal to said objective lens assembly.

16. A video otoscope as recited in claim 15, including video processing means for processing an electrical signal generated by said electronic sensor into a video signal, and video display means for displaying said processed signal.

17. A video otoscope as recited in claim 15, including illumination means having a source of illumination and light transmittance means for transmitting light from said source of illumination to the distal tip opening of said frusto-conical extension.

18. A video otoscope as recited in claim 17, wherein said light transmittance means includes a bundle of optical fibers circumferentially fanned out in an annular space between said inner housing and said frusto-conical extension, said bundle of fibers having light emitting ends disposed in a ring-like configuration at the tip opening of said extension.

19. A video otoscope as recited in claim 18, wherein said insufflation means includes at least one second port extending through said frusto-conical extension into the interior of said body portion, said at least one second port being separately disposed from said tip opening to allow air projected through into said interior from said first port to be directed to the speculum tip opening.

20. A video otoscope as recited in claim 19, wherein said insufflation means includes at least one hollow tubular member sized for fitting within said at least one second port and extending rearwardly toward said first port for directing air therefrom toward said speculum tip opening.

21. A video otoscope as recited in claim 20, wherein said at least one second port is proximally located along said frusto-conical extension so as to allow said at least one tubular member to be inserted therethrough into the interior of said body portion without contacting said electronic sensor and said inner housing.

22. A video otoscope as recited in claim 18, wherein said bundle of optical fibers includes at least one discontinuous portion extending rearwardly from the extension tip opening into the interior of said body portion, said at least one discontinuous portion forming a channel in said annular space for allowing insufflating air entering said interior from said first port to be directed therethrough.

23. A video otoscope as recited in claim 22, wherein said ring of optical fibers includes a pair of equally spaced discontinuous portions.

24. A video otoscope as recited in claim 23, including at least one tubular member for fitting in at least one of said discontinuous portions, said at least one tubular member extending rearwardly from said tip opening of said extension into the interior of said body portion for allowing air directed into said interior from said first port to be directed therethrough.

25. A video otoscope as recited in claim 22, including a hollow tubular member sized for fitting in at least one discontinuous portion, said tubular member extending rearwardly toward said first port for allowing air from said first port to be directed therethrough.

26. A video otoscope as recited in claim 2, including illuminating means for illuminating a target being viewed through said distal tip openings, said illuminating means including a source of illumination and light transmittance means for transmitting light form said source of illumination to said frusto-conical extension.

27. A video otoscope as recited in claim 26, wherein said light transmittance means includes said attached speculum, said speculum being made of a light transmissive material for allowing light to be transmitted from said source of illumination to a distal end of said speculum.

28. A video otoscope as recited in claim 27, wherein said speculum is made from a transparent material.

29. A video otoscope as recited in claim 27, wherein said speculum is made optically diffuse so as to allow uniformity of illumination at said distal tip.

30. A video otoscope as recited in claim 27, wherein said speculum comprises polycarbonate.

31. A video otoscope as recited in claim 27, wherein said optical system includes a rod lens assembly including a distal rod lens end extending from said frusto-conical extension, said speculum being placed in overlaying relation to said frusto-conical extension wherein the speculum tip opening is substantially coterminous with a distal end of said extending rod end.

32. A video otoscope as recited in claim 31, wherein said light transmittance means includes a plurality of optical fibers having emitting ends circumferentially arranged in the tip opening of said frusto-conical extension, said speculum having a circular portion, which when said speculum is attached to said extension is adjacently positioned relative to said arranged light emitting ends.

33. A video otoscope as recited in claim 32, wherein said circular portion includes a circumferential edge having a diameter substantially equal to the diameter of the tip opening of said extension for allowing to be transmitted from said light emitting ends through said speculum.

34. An otoscope for examining the interior of an ear canal, said otoscope comprising:
   a body portion having a defined interior and respective open distal and proximal ends;
   illumination means including a source of illumination and light transmittance means for transmitting light from said source of illumination to the distal end of said body portion;
   a speculum mounted to said distal end for insertion into said ear canal, said speculum having a frusto-conical body including a distal end having a tip opening, said body portion including viewing means axially aligned with the tip opening of said speculum to allow viewing of a target therethrough when said speculum is attached, wherein said speculum is made from a light transmissive material allowing light from said distal end to be further transmitted from said light transmittance means through the body of said speculum to the distal end of said speculum for illuminating said target, and
   insufflation means for directing air through the distal tip opening of said speculum for stimulating the tympanic membrane in the ear canal.

35. An otoscope as recited in claim 34, wherein said insufflation means includes a first port located on said body portion sized for allowing attachment thereto by a depressible pneumatic bulb, said bulb being capable of projecting air under pressure into the interior of said body portion.

36. An otoscope as recited in claim 35, wherein said body portion includes a frusto-conical extension depending from said distal end, said extension having a distal tip opening axially aligned with said viewing means and said speculum tip opening.

37. An otoscope as recited in claim 36, wherein said insufflation means includes at least one second port extending though said conical extension into the interior of said body portion, said at least one second port being separately disposed on said conical extension from the tip opening to allow air projected into said interior from said first port to be directed toward said speculum tip opening.

38. An otoscope as recited in claim 37, including at least one tubular member sized for fitting within said at least one second port and extending rearwardly toward said first port for directing air therefrom toward the speculum tip opening.

39. An otoscope as recited in claim 36, wherein said viewing means includes an optical system including at least one optical element disposed in the tip opening of said conical extension, said light transmittance means including a bundle of optical fibers, said bundle of optical fibers including light emitting ends fanned out into in a ringlike configuration around said optical system in the extension tip opening.

40. An otoscope as recited in claim 39, including sealing means for sealing said bundle of optical fibers together for preventing the passage of air therethrough.

41. An otoscope as recited in claim 39, wherein said ring of optical fibers includes at least one discontinuous portion extending rearwardly into the interior of said body portion, said at least one discontinuous portion forming a channel for allowing insufflated air to be directed through the tip opening of said extension.

42. An otoscope as recited in claim 41, wherein said ring of optical fibers includes a pair of equally spaced discontinuous portions.

43. An otoscope as recited in claim 42, including at least one tubular member for fitting in at least one of said discontinuous portions, said at least one tubular member extending rearwardly from said tip opening of said conical extension toward said first port for directing insufflating air therethrough.

44. An otoscope as recited in claim 41, including a tubular member sized for fitting in said at least one discontinuous portion, said tubular member extending rearwardly from said tip opening of said extension toward said first port for directing insufflating air therethrough.

45. An otoscope as recited in claim 34, wherein said light transmittance means includes a bundle of optical fibers extending from said source of illumination, said bundle of fibers including light emitting ends arranged in a ring-like configuration at said distal end, wherein said speculum includes a circular portion adjacently arranged to said light emitting ends when said speculum is attached thereto.

46. An otoscope as recited in claim 45, wherein said body portion includes a frusto-conical extension extending from said distal end, said extension having a tip opening axially aligned with said speculum tip opening and said viewing means, wherein said bundle of optical fibers extends from said source of illumination through said extension, said light emitting ends being arranged at said extension tip opening, and in which said tip opening is disposed adjacent to said circular portion on said speculum for allowing light to be transmitted to the distal end of said speculum.

47. An otoscope as recited in claim 34, wherein said speculum is made from a substantially transparent material.

48. An otoscope as recited in claim 34, wherein said speculum is made from a diffuse optical material for uniformly transmitting light therethrough.

49. An otoscope as recited in claim 34, wherein said speculum comprises a polycarbonate material.

50. An otoscope as recited in claim 34, further comprising electronic imaging means, wherein said viewing means includes an optical system including at least one optical element for focussing an optical image of a target viewed through said distal tip openings onto said electronic imaging means.

51. An otoscope as recited in claim 50, including insufflation means for directing air through the distal end opening of said speculum for stimulating the tympanic membrane in the ear canal.

52. An otoscope as recited in claim 51, wherein said insufflation means includes a first port located on said body portion sized for allowing attachment thereto by a depressible pneumatic bulb, said bulb being capable of projecting air under pressure into the interior of said body portion.

53. An otoscope as recited in claim 52, including a frusto-conical extension depending from said distal end, said extension having a distal tip opening axially aligned with said viewing means and said speculum tip opening, said extension having means for supporting said speculum thereto.

54. An otoscope as recited in claim 53, wherein said insufflation means includes at least one second port extending though said frustoconical extension into the interior of said body portion, said at least one second port being separately disposed on said frusto-conical extension from the tip opening to allow air projected into said interior from said first port to be directed toward said speculum tip opening.

55. An otoscope as recited in claim 54, including at least one tubular member sized for fitting within said at least one second port and extending rearwardly toward said first port for directing air therefrom toward the speculum tip opening.

56. An otoscope as recited in claim 53, wherein said light transmittance means includes a bundle of optical fibers, said bundle of optical fibers including light emitting ends fanned out into a ring-like configuration around said optical system in the tip opening of said frusto-conical extension.

57. An otoscope as recited in claim 56, including sealing means for sealing said bundle of optical fibers together for preventing the passage of air therethrough.

58. An otoscope as recited in claim 56, wherein said ring of optical fibers includes at least one discontinuous portion extending rearwardly into the interior of said body portion, said at least one discontinuous portion forming a channel for allowing insufflated air to be directed through the tip opening of said extension.

59. An otoscope as recited in claim 58, wherein said ring of optical fibers includes a pair of equally spaced discontinuous portions.

60. An otoscope as recited in claim 59, including at least one tubular member for fitting in at least one of said discontinuous portions, said at least tubular member extending rearwardly from said tip opening of said extension toward said first port for directing insufflating air therethrough.

61. An otoscope as recited in claim 58, including a tubular member sized for fitting in said at least one discontinuous portion, said tubular member extending rearwardly from said tip opening of said extension toward said first port for directing insufflating air therethrough.

62. An otoscope as recited in claim 50, wherein said electronic imaging means includes an electronic sensor, said sensor being disposed in the interior of said body portion.

63. An otoscope as recited in claim 62, wherein said electronic sensor is distally disposed within said frusto-conical extension.

64. An otoscope for examining the interior of the ear canal, said otoscope comprising:

a body portion including an interior and opposite proximal and distal ends, said distal end including a frusto-conical distal extension having a distal tip opening;

a speculum releasably mounted to said distal end in overlaying fashion with said extension, said speculum having a frusto-conical shape including a distal tip opening axially aligned with the tip opening of said extension, said speculum being sized for insertion to only a predetermined distance into the ear canal;

viewing means for viewing a target of interest through said aligned distal tip openings along a defined viewing axis;

illumination means including a source of illumination and light transmittance means for transmitting light from said source of illumination to said distal end; and insufflation means for projecting air through the tip opening of said speculum, said insufflation means including a first port located on said body portion for allowing attachment thereto by a depressible pneumatic bulb capable of projecting air into the interior of said body portion, in which said insufflation means includes at least one second port extending through said distal extension of said body portion, said at least one second port for projecting air entering said interior from said first port through the tip opening of said speculum, said at least one second port disposed on the conical extension.

65. An otoscope as recited in claim 64, wherein said speculum is made from a light transmissive material for allowing light to be transmitted from said distal end to the tip end of said speculum.

66. An otoscope as recited in claim 64, including at least one tubular member sized for fitting within said at least one second port, said tubular member extending rearwardly toward said first port for directing insufflating air therefrom toward the tip opening of said speculum.

67. An otoscope as recited in claim 64, including video imaging means disposed proximally along said viewing axis for receiving an optical image from said viewing means.

68. An otoscope as recited in claim 67, wherein said video imaging means includes an electronic imager disposed distally within said extension, said viewing means including at least one objective lens for focussing an optical image on said electronic imager.

69. An otoscope as recited in claim 67, wherein said video imaging means includes an electronic sensor, said otoscope further comprising video processing means for processing an electrical signal from said electronic sensor, and video display means for displaying said processed signal, wherein said viewing means includes at least one optical element for focussing an optical image viewed along a viewing axis through said tip openings onto said electronic sensor.

70. An otoscope for examining the interior of the ear canal, said otoscope comprising:

a body portion including an interior and opposite proximal and distal ends, said distal end including a frusto-conical distal extension having a distal tip opening;

a speculum releasably mounted to said distal end in overlaying fashion with said extension, said speculum having a frusto-conical shape including a distal tip opening axially aligned with the tip opening of said extension, said speculum being sized for insertion to only a predetermined distance into the ear canal;

viewing means for viewing a target of interest through said aligned distal tip openings along a defined viewing axis;

illumination means including a source of illumination and light transmittance means for transmitting light from said source of illumination to said distal end, said light transmissive means including a bundle of optical fibers having light emitting ends arranged circumferentially in a ring-like configuration in the tip opening of said extension; and insufflation means for projecting air through the tip opening of said speculum, said insufflation means including a first port located on said body portion for allowing attachment thereto by a depressible pneumatic bulb capable of projecting air into the interior of said body portion, wherein said ring-like configuration has at least one discontinuous portion extending rearwardly toward said first port for allowing air to be projected therethrough.

71. An otoscope as recited in claim 70, including at least one tubular member sized for fitting in said at least one discontinuous portion and extending rearwardly toward said first port.

72. An otoscope as recited in claim 70, including a pair of equally spaced discontinuous portions, each said portion defining a channel for allowing air from said first port to be directed for exhaust through said tip opening of said extension.

73. An otoscope as recited in claim 72, including a corresponding tubular member sized for fitting in at least one of said discontinuous portions and extending rearwardly from said tip opening for guiding air entering said interior from said first port.

74. An otoscope as recited in claim 70, including sealing means for preventing air from exiting said body portion other than through said at least one discontinuous portion.

75. An otoscope as recited in claim 70, including an electronic sensor, video processing means for processing an electrical signal from said electronic sensor, and video display means for displaying said processed signal, wherein said viewing means includes at least one optical element for focussing an optical image viewed along a viewing axis through said tip openings onto said electronic sensor.

* * * * *